United States Patent
Gineys et al.

(10) Patent No.: US 12,303,867 B2
(45) Date of Patent: May 20, 2025

(54) SOL-GEL MATERIAL ABSORBING ALDEHYDES AND KETONES, AND THE PROCESS FOR ITS PREPARATION

(71) Applicant: SEB S.A., Ecully (FR)

(72) Inventors: Mickael Gineys, La Mure (FR); Frederic Hammel, La Ciotat (FR); Denis Paccaud, Lyons (FR); Mathilde Sibeaud, Lyons (FR); Marie-Pierre Som, Montelier (FR)

(73) Assignee: SEB S.A. (FR)

( * ) Notice: Subject to any disclaimer, the term of this patent is extended or adjusted under 35 U.S.C. 154(b) by 1079 days.

(21) Appl. No.: 17/252,889

(22) PCT Filed: Jul. 10, 2019

(86) PCT No.: PCT/EP2019/068512
§ 371 (c)(1),
(2) Date: Dec. 16, 2020

(87) PCT Pub. No.: WO2020/020639
PCT Pub. Date: Jan. 30, 2020

(65) Prior Publication Data
US 2021/0178364 A1   Jun. 17, 2021

(30) Foreign Application Priority Data

Jul. 27, 2018 (EP) ..................................... 18186191
Jan. 28, 2019 (EP) ..................................... 19154042

(51) Int. Cl.
*B01J 20/26* (2006.01)
*A61L 9/014* (2006.01)
(Continued)

(52) U.S. Cl.
CPC ............. *B01J 20/262* (2013.01); *A61L 9/014* (2013.01); *B01D 53/02* (2013.01); *B01J 20/103* (2013.01);
(Continued)

(58) Field of Classification Search
CPC ...... A61L 9/014; A61L 9/048; A61L 2209/22; B01D 53/02; B01D 2253/20;
(Continued)

(56) References Cited

U.S. PATENT DOCUMENTS 7,807,752 B2 * 10/2010 Masutani ................. C09D 5/00
                                                                  525/104
9,993,801 B2 *  6/2018 Sugiura .................... B01J 20/06
(Continued)

FOREIGN PATENT DOCUMENTS

EP    2615125 A1    7/2013
EP    3045224 A1    7/2016
(Continued)

OTHER PUBLICATIONS

Escalettes et al. WO2016046498A1 English Translation (Year: 2016).*
(Continued)

*Primary Examiner* — Brian D Walck
*Assistant Examiner* — Jordan W Taylor
(74) *Attorney, Agent, or Firm* — Lerner David LLP

(57) ABSTRACT

The present invention concerns an adsorbent porous sol-gel material comprising at least-silane oxides;—an inorganic and/or organic acid with a boiling temperature higher than 100° C.;—a molecular probe of general formula (I) or one of the salts of same in which $R_1$, $R_2$, $R_3$, $R_4$, $R_5$, $R_6$ separately represent a hydrogen atom, a (C1-C6) alkyl group, a (C3-C7) cycloalkyl group, an alkyl-(C3-C7) cycloalkyl group; in which Z represents a spacer group
(Continued)

chosen from a (C1-C16) alkyl group, a (C2-C16) alkenyl group, a (C2-C16) alkynyl group, a (C1-C16) halogenoalkyl group, an aryl group, an aryloxy group, a carbocycle group, or an aryl-(C1-C16) alkyl group.

3 Claims, 1 Drawing Sheet

(51) Int. Cl.
    *B01D 53/02*     (2006.01)
    *B01J 20/10*     (2006.01)
    *B01J 20/22*     (2006.01)
    *B01J 20/28*     (2006.01)
    *B01J 20/30*     (2006.01)

(52) U.S. Cl.
    CPC ......... *B01J 20/22* (2013.01); *B01J 20/28019* (2013.01); *B01J 20/28047* (2013.01); *B01J 20/3007* (2013.01); *B01J 20/3057* (2013.01); *B01J 20/3085* (2013.01); *A61L 2209/22* (2013.01); *B01D 2253/202* (2013.01); *B01D 2257/704* (2013.01); *B01D 2257/708* (2013.01); *B01D 2259/4508* (2013.01)

(58) Field of Classification Search
    CPC ........ B01D 2253/202; B01D 2257/704; B01D 2257/708; B01D 2258/06; B01D 2259/4508; B01J 20/103; B01J 20/22; B01J 20/262; B01J 20/28019; B01J 20/28047; B01J 20/3007; B01J 20/3057; B01J 20/3078; B01J 20/3085
See application file for complete search history.

(56) References Cited

U.S. PATENT DOCUMENTS

| | | | |
|---|---|---|---|
| 2004/0091411 A1* | 5/2004 | Modrek-Najafabadi | ............ B01J 20/3078 423/338 |
| 2008/0220534 A1 | 9/2008 | Paolacci et al. | |
| 2014/0242713 A1 | 8/2014 | Crunaire et al. | |
| 2017/0296967 A1 | 10/2017 | Escalettes et al. | |
| 2018/0177906 A1* | 6/2018 | Sugiura | ............ A61L 9/014 |

FOREIGN PATENT DOCUMENTS

| | | | | |
|---|---|---|---|---|
| FR | 2890745 A1 | 3/2007 | | |
| JP | 2010235363 A | 10/2010 | | |
| JP | 2017160356 A | 9/2017 | | |
| WO | WO-2004058311 A1 * | 7/2004 | ............... | A61L 9/01 |
| WO | WO-2007074816 A1 * | 7/2007 | ............... | A61L 9/01 |
| WO | WO-2016046498 A1 * | 3/2016 | ......... | B01D 46/0008 |
| WO | WO-2016167258 A1 * | 10/2016 | ............... | A61L 9/01 |

OTHER PUBLICATIONS

Kishida et al. WO2016167258A1 Google Patents Translation (Year: 2016).*
Descamps et al. Sensors and Actuators B 2012, 170, 104-108 (Year: 2012).*
Ganga et al. (J. Molecular Catalysis A, Chemical 2016, 420, 264-271) (Year: 2016).*
Nakano et al. (WO2007074816A1; English Machine Translation) (Year: 2007).*
Hirukawa et al. (WO2004058311A1; English Machine Translation) (Year: 2004).*
International Search Report for PCT/EP2019/068512 mailed Sep. 11, 2019; 3 pages.

* cited by examiner

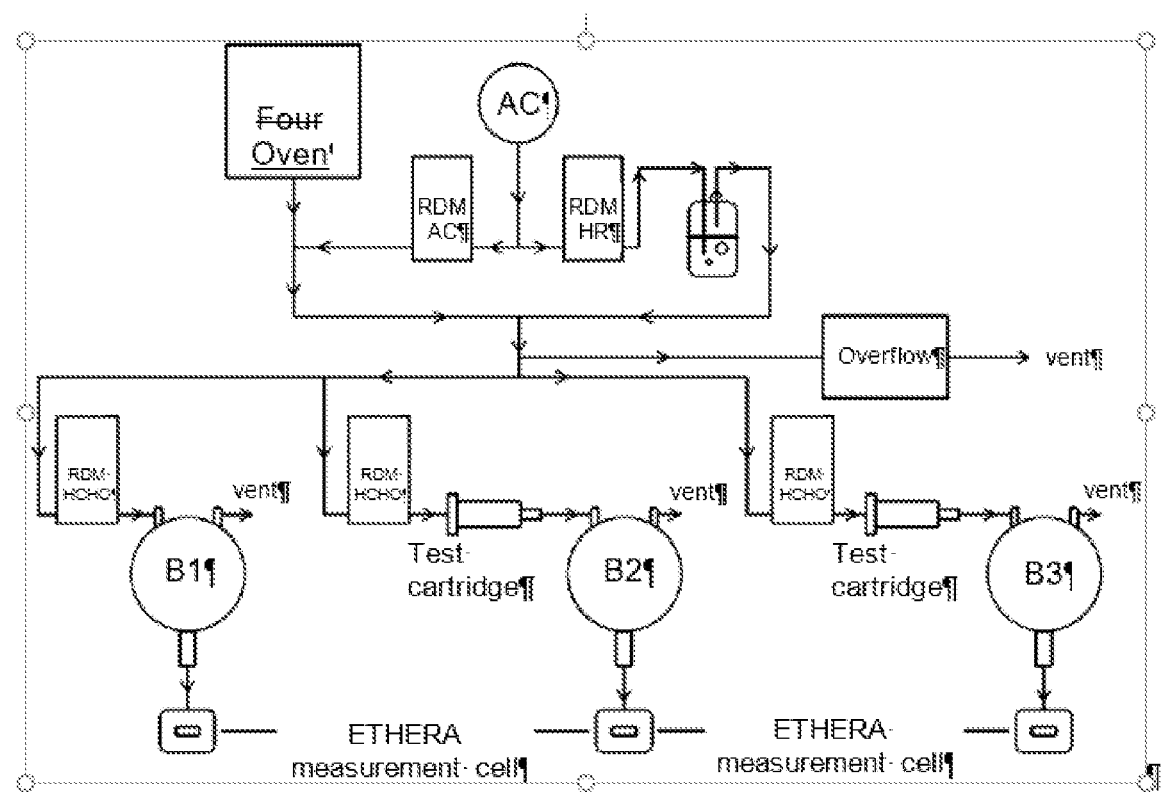

SOL-GEL MATERIAL ABSORBING ALDEHYDES AND KETONES, AND THE PROCESS FOR ITS PREPARATION

CROSS REFERENCE TO RELATED APPLICATIONS

The present application is a national phase entry under 35 U.S.C. § 371 of International Application No. PCT/EP2019/068512 filed Jul. 10, 2019, published in French, which claims priority from European Patent Application Nos. 18186191.5 filed Jul. 27, 2018 and 19154042.6, filed Jan. 28, 2019 all of which are incorporated herein by reference.

The invention concerns a sol-gel material adsorbing aldehydes and ketones, the process for its preparation, its uses and an air purification device using this material.

Aldehydes are among the most abundant household chemical pollutants. Its sources are numerous. In particular, they can be related to external productions such as the photo-oxidation of methane. However, the main sources of aldehyde emissions are inside the home and are very diverse: resins and glues used to make chipboard, particle board and plywood, textile coatings, wallpaper, paints, leather, urea-formaldehyde insulating foams used as thermal insulation injected into walls and partitions.

Formaldehyde is also a preservative, disinfectant and dehydrating agent. That is why it is widely used as a solvent in hospitals for the disinfection of surgical instruments but also in the funeral services industry where thanatopraxy is practiced.

Given the harmful effects of such chemical pollutants on public health, it seems necessary to ensure the purification of ambient air in residential buildings by reducing the aldehyde content, in particular formaldehyde, and by offering new depollution devices.

The treatment and purification of air by adsorption using adsorbent materials is well-known. This is a surface phenomenon whereby air pollutants such as atoms, ions or molecules (adsorbates) attach themselves to the solid surface of the adsorbent material. This attachment can be:

either physical, involving weak bonds of the Van der Waals force type between the adsorbed chemical species and the adsorbent, or chemical, involving high binding energies such as covalent, ionic or metallic bonds between the adsorbed chemical species and the adsorbent.

The opposite phenomenon, whereby molecules adsorbed on a surface become detached from it, for example as a result of a temperature increase or a drop in pressure, is known as desorption.

It is possible to make a material adsorbent by attaching a probe molecule capable of trapping the pollutant onto this material and retaining it without degrading it. The material is generally porous, preferably microporous, are even more preferably nanoporous, with a large specific surface area. The probe molecule is generally deposited onto the material by impregnation to facilitate surface phenomena in the porous structure of the material.

According to document FR 2890745 there is known porous material for the removal of aldehydes and more precisely formaldehyde which is a nanoporous matrix of metal oxides comprising at least one aldehyde-reactive function. The probe molecules described are enaminones and the corresponding 3-diketone/amine pairs, imines and hydrazines, or salts derived from these compounds.

It has, however, been observed that these materials show a decrease in their mechanical resistance and a migration of the probe molecule in humid or even tropical atmospheres. Thus in a humid atmosphere (about 60-80% relative humidity (RH) or more), these materials become brittle and crumble. In addition, the probe molecule tends to escape from the porous material and is released into its environment, as the material loses its ability to trap pollutants.

Hence the present invention attempts to solve all or part of the above-mentioned drawbacks, in particular by proposing a process for the preparation of a porous adsorbent material with improved mechanical resistance and without migration of the probe molecule in a tropical atmosphere (e.g. at about 80% relative humidity), while advantageously presenting a reduced quantity of probe molecule in the material.

Unexpectedly, the inventors have demonstrated that it is possible to use certain organic acids and probe molecules to make a nanoporous sol-gel material that adsorbs aldehydes and ketones to side-step the above disadvantages.

The Invention Provides at Least One of the Determining Advantages Described Below:

definitively and irreversibly traps pollutants from the ambient air by adsorption of pollutants; whereas with conventional adsorbent materials such as zeolites or activated carbon in particular, the pollutants are likely to be released;

attach the probe molecule in the sol-gel material and prevent the migration of this probe molecule into the ambient air, especially in tropical or high humidity atmospheres (e.g. at about 60-80% relative humidity);

improve the mechanical resistance of the material in tropical or high humidity conditions; and present a material with a reduced quantity of the probe molecule attached in the material with a similar trapping performance.

Other advantages and characteristics of the invention will clearly emerge upon reading the description and examples to follow, given purely for illustrative purposes and which are not exhaustive.

To this end, the invention makes use of a process for the preparation of a porous sol-gel adsorbent material comprising the following successive steps:

i) preparing an aqueous composition comprising at least
an alkoxysilane type sol-gel precursor;
an inorganic and/or organic acid having a boiling temperature of more than 100° C.;
a probe molecule with a general formula (I) or one of its salts

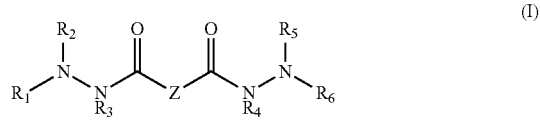

where $R_1$, $R_2$, $R_3$, $R_4$, $R_5$, $R_6$ independently represents a hydrogen atom, a (C1-C6) alkyl group, a (C3-C7) cycloalkyl group or an alkyl-(C3-C7) cycloalkyl group; with Z representing a spacer group selected from a (C1-C16) alkyl group, a (C2-C16) alkenyl group, a (C2-C16) alkynyl group, a (C1-C16) haloalkyl group, an aryl group, an aryloxy group, a carbocyclic group and an aryl-(C1-C16) alkyl group;

ii) cast the composition obtained in step i) and apply a heat treatment at a temperature above 20° C. so that the hydrolysis/condensation reaction occurs;

iii) dry the sol-gel adsorbent material obtained.

Generally, a sol-gel process uses metal alkoxides of formula M (OR) xR'n-x as precursors, where M is a metal, specifically silicon, R is an alkyl group and R' a group carrying one or more functions where n=4 and x can vary between 2 and 4. In the presence of water, the alkoxy groups (R—O) are hydrolyzed into silanol groups (Si—OH). These condense to form siloxane bonds (Si—O—Si—). This is the hydrolysis/condensation reaction.

The process for the preparation of porous adsorbent sol-gel material according to the invention uses an alkoxysilane-type sol-gel precursor. This alkoxysilane-type sol-gel precursor is preferably from selected tetramethyl orthosilicate (TMOS), methyltrimethoxysilane (MTMS), tetraethoxysilane (TEOS), methyltriethoxysilane (MTES), dimethyldimethoxysilane and mixtures thereof, preferably tetramethyl orthosilicate, also called tetramethoxysilane.

The gel synthesis in step i) is advantageously carried out using tetramethoxysilane or a mixture of tetramethoxysilane and at least one other organosilicon-precursor selected from phenyltrimethoxysilane, phenyltriethoxysilane, fluoroalkyltrimethoxysilane, fluoroalkyltriethoxysilane, chloroalkyltrimethoxysilane, chloroalkyltriethoxysilane, alkyltrimethoxysilane, alkyltriethoxysilane, aminopropyltriethoxysilane and mixtures thereof.

The gel synthesis in step i) is preferably carried out using tetramethoxysilane or a mixture of tetramethoxysilane and at least one other organosilicon precursor selected from chloroalkyltrimethoxysilane, chloroalkyltriethoxysilane, aminopropyltriethoxysilane and mixtures thereof.

The gel synthesis in step i) is preferably carried out using tetramethoxysilane or a mixture of tetramethoxysilane and at least one other organosilicon precursor selected from chloropropyltrimethoxysilane, chloropropyltriethoxysilane, (C3-C10) alkyltrimethoxysilane, (C3-C10) alkyltriethoxysilane, aminopropyltriethoxysilane and mixtures thereof.

More preferably, the gel synthesis in step i) is carried out using tetramethoxysilane or a mixture of tetramethoxysilane and at least one other organosilicon precursor selected from propyltrimethoxysilane, propyltriethoxysilane, propyltrimethoxysilane, chloropropyltrimethoxysilane, chloropropyltriethoxysilane, aminopropyltriethoxysilane and mixtures thereof.

More preferably, the gel synthesis in step i) is carried out using tetramethoxysilane or a mixture of tetramethoxysilane and at least one other organosilicon precursor selected from chloropropyltrimethoxysilane and an aminopropyltriethoxysilane, even more preferably chosen from (3-chloropropyl) trimethoxysilane (CITMOS), and (3-aminopropyl) triethoxysilane (APTES).

Yet more preferably, step i) is carried out using tetramethoxysilane or a mixture of tetramethoxysilane and (3-chloropropyl) trimethoxysilane (CITMOS), or a mixture of tetramethoxysilane and (3-aminopropyl) triethoxysilane (APTES).

The process for the preparation of a porous sol-gel adsorbent material according to the invention uses a probe molecule of general formula (I) or one of its salts.

For the purposes of this invention, a "(C1-C6) alkyl" group is to be understood as a saturated monovalent hydrocarbon chain, linear or branched, containing 1 to 6, preferably 1 to 4, carbon atoms. Examples include methyl, ethyl, propyl, isopropyl, butyl, isobutyl, sec-butyl, tert-butyl, pentyl and hexyl groups.

For the purposes of this invention, a "(C3-C7) cycloalkyl" group is to be understood as a cyclic saturated hydrocarbon chain containing 3 to 7 ring carbon atoms. Examples are cyclopropyl, cyclopentyl, cyclohexyl and cycloheptyl groups.

For the purposes of this invention, "alkyl-(C3-C7) cycloalkyl" is to be understood as a (C3-C7) cycloalkyl group as defined above, linked to the rest of the molecule via a (C1-C6) alkyl chain as defined above.

For the purposes of this invention, a "(C1-C16) alkyl" group is to be understood as a saturated monovalent hydrocarbon chain, linear or branched, comprising 1 to 16, preferably 1 to 10, more preferably 1 to 8 carbon atoms.

For the purposes of this invention, a "(C2-C16) alkenyl" group is to be understood as a monovalent hydrocarbon chain, linear or branched, containing at least one double bond and comprising 2 to 16 carbon atoms. Examples include ethynyl or allyl groups.

For the purposes of this invention, a "(C2-C16) alkynyl" group is to be understood as a monovalent hydrocarbon chain, linear or branched, containing at least one triple bond and comprising 2 to 16 carbon atoms. Examples include ethynyl or propynyl groups.

For the purposes of this invention, "(C1-C16) haloalkyl" is to be understood as a (C1-C16) alkyl group, as defined above, in which one or more hydrogen atoms have been replaced by a halogen atom as defined below. In particular, it can be a CF3 group.

For the purposes of this invention, "halogen atom" means fluorine, chlorine, bromine or iodine atoms.

For the purposes of this invention, "aryl" is to be understood as an aromatic hydrocarbon group, preferably containing from 6 to 10 carbon atoms, and comprising one or more adjacent rings, such as, for example, a phenyl or naphthyl group. Advantageously, it is phenyl.

For the purposes of this invention, the term "aryloxy group" means any aryl group as defined above which is bonded to the rest of the molecule via at least one oxygen atom. In particular, it can be a phenyloxy group.

For the purposes of the present invention, "carbocycle" is to be understood as a saturated, unsaturated or aromatic monocyclic or polycyclic hydrocarbon system comprising from 3 to 12 carbon atoms. The polycyclic system comprises at least 2, specifically 2 or 3 linked or bridged cycles. Each cycle of the monocyclic or polycyclic system advantageously comprises 3 to 8, specifically 4 to 7 and especially 5 or 6 carbon atoms. Examples are adamantyl, cyclohexyl, cyclopentyl, cyclopropyl, cyclohexenyl, phenyl, naphthyl.

For the purposes of this invention, "aryl-(C1-C6) alkyl" is to be understood as an aryl group as defined above, linked to the rest of the molecule via a (C1-C6) alkyl chain as defined above. The benzyl group is on example.

Preferably, the process for preparing a porous sol-gel adsorbent material according to the invention uses a probe molecule of general formula (I) with $R_1$, $R_2$, $R_3$, $R_4$, $R_5$, $R_6$ representing a hydrogen atom or a (C1-C6) alkyl group.

Preferably, the process for the preparation of a porous sol-gel adsorbent material according to the invention uses a probe molecule of general formula (I) while Z represents a (C1-C16) alkyl group, preferably a (C1-C10) alkyl group, or a C4, C6 or C8 alkyl group.

Preferably, the process for preparing a porous sol-gel adsorbent material according to the invention uses a probe molecule of general formula (I) while Z represents an aryl group or an aryl-(C1-C6) alkyl group.

Preferably, the process for preparing a porous sol-gel adsorbent material according to the invention uses a probe molecule of general formula (I) with $R_1$, $R_2$, $R_3$, $R_4$, $R_5$, $R_6$ representing a hydrogen atom or a (C1-C6) alkyl group, while Z represents a (C1-C16) alkyl group, preferably a (C1-C10) alkyl group, or a C4, C6 or C8 alkyl group.

Preferably, the process for preparing a porous sol-gel adsorbent material according to the invention uses a probe molecule of general formula (I) with $R_1$, $R_2$, $R_3$, $R_4$, $R_5$, $R_6$ representing a hydrogen atom or a (C1-C6) alkyl group, while Z represents an aryl group or an aryl-(C1-C6) alkyl group.

According to the invention, it is possible to combine the different groups of the probe molecule of general formula (I).

Preferably, the method for the preparation of a porous sol-gel adsorbent material according to the invention uses a probe molecule or its salt which is adipic acid dihydrazide ($C_6H_{14}N_4O_2$),

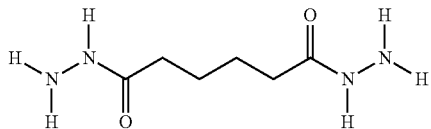 [SMILES: NNC(=O)CCCCC(=O)NN]

sebacic acid dihydrazide ($C_{10}H_{22}N_4O_2$)

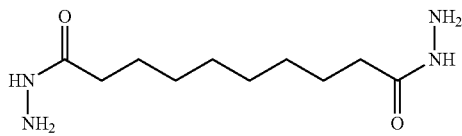 [SMILES: NNC(=O)CCCCCCCCC(=O)NN]

terephthalic acid dihydrazide ($C_8H_{10}N_4O_2$).

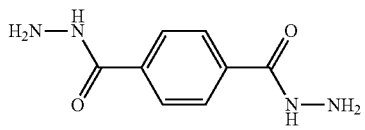 [SMILES: NNC(=O)c1ccc(C(=O)NN)cc1]

Since the amine function of the probe molecule is a basic functional group, it can be in the form of salts. The salts specifically include the acid addition salts of the probe molecule.

The manufacturing process of the adsorbent porous sol-gel material according to the invention allows the introduction of the probe molecule during its preparation, i.e. in-situ or one-pot, and not by impregnation, i.e. not by bringing a liquid into contact with a solid or semi-solid. Advantageously, this is a synthesis of the gel in step i) of the monotope synthesis type. Monotope synthesis or one-pot synthesis is generally a chemical synthesis in which a reagent undergoes several reactions in a single reaction mixture (a single reactor, for example). In other words, the synthesis is carried out in a single step with an alkoxysilane-type sol-gel precursor, e.g. tetramethoxysilane or a mixture of tetramethoxysilane and another organosilicon precursor, and the probe molecule(s) in the presence of the inorganic and/or organic acid and water and possibly a polar organic solvent. That means that there is no impregnation of the probe molecule on the sol-gel material after completion of its manufacture, but a close combination of materials during the preparation of the sol-gel. Advantageously, the combination of the probe molecule with a sol-gel precursor of the alkoxysilane type takes place in a liquid or semi-liquid state.

Advantageously, the process according to the invention, using a monotope synthesis saves time and increases the overall chemical yield.

The manufacturing process of the adsorbent porous sol-gel material according to the invention allows advantageously the reduction of the quantities of probe molecules compared to the processes by impregnation. Saturation of the specific surface by impregnation methods is thus avoided.

It should be pointed out that the process for preparing a porous sol-gel adsorbent material according to the invention is not a process using the impregnation or immersion of the probe molecule.

In one embodiment, the porous sol-gel adsorbent material according to the invention contains neither zeolite nor activated carbon.

When using a mixture of tetramethoxysilane and another organosilicon precursor, the molar proportions of tetramethoxysilane/other organosilicon precursor may vary from 1/0.01 to 1/0.2, preferably from 1/0.01 to 1/0.04.

The aqueous composition used in step i) of the process according to the invention comprises an alkoxysilane precursor/probe molecule molar ratio that ranges from 1/0.1 to 1/0.001, preferably from 1/0.08 to 1/0.002, more preferably from 1/0.075 to 1/0.010, and in particular a ratio equal to 1/0.05 or 1/0.015.

The aqueous composition used in step i) of the process according to the invention comprises a TMOS/probe molecule molar ratio ranging from 1/0.1 to 1/0.001, preferably from 1/0.08 to 1/0.002, more preferably from 1/0.075 to 1/0.010, and in particular a ratio equal to 1/0.05 or 1/0.015.

The gel synthesis in step i) is advantageously carried out in an aqueous medium in the presence of an inorganic and/or organic acid having a boiling temperature greater than or equal to 100° C., preferably greater than or equal to 150° C., more preferably greater than or equal to 180° C. In particular, the acid used according to the process of the invention is an acid with a high non-volatility.

The gel synthesis in step i) is advantageously carried out in an aqueous medium in the presence of an acid, preferably an acid with a pKA of at most 3.5, preferably at most 2.8.

The acid is preferably an inorganic and/or organic acid chosen among sulphamic acid, phosphoric acid, paratoluenesulphonic acid, parahydroxybenzoic acid and mixtures thereof.

In particular, the acid used in the invention process is a weak hygroscopic acid.

When the synthesis takes place in an acidic medium it is possible to obtain better color performances of the sol-gel matrix when the probe molecule, and in particular its amine group, reacts with aldehydes and/or ketones. Good performances are obtained when the pH of the aqueous medium is less than 3, preferably less than 2, more preferably less than 2.5, more preferably less than 2.2 and even more preferably less than 1.8.

The gel synthesis in step i) is carried out in an aqueous medium. Advantageously, the aqueous medium is water or a mixture of water and possibly a polar organic solvent. The polar organic solvent can be a protic organic solvent, preferably a C1 to C6 aliphatic alcohol, more preferably methanol or ethanol. The person skilled in the art will be able to easily determine the necessary quantities of water and possibly polar organic solvent depending on the organosilicon precursor(s) used.

The process includes a step ii) of casting the aqueous composition obtained in step i). For example, it involves depositing or pouring this composition, preferably liquid or semi-liquid, into a container that will give it its shape.

The process includes a step iii) that involves drying the sol-gel material obtained after step ii). This step involves the evaporation of the water contained in the material. This can be done at room temperature over an extended period of time of a few days either under heat or not.

According to an embodiment of the process according to the invention, it includes a step iv) involving firing the sol-gel material in addition to step iii) that involves drying. This additional step of cooking the sol-gel adsorbent material after it has been produced can take place at a temperature of 50 to 150° C., preferably 60 to 80° C. and in particular at 70° C.

Another subject of the invention is the material likely to be obtained through the process according to the invention.

Another subject of the invention is obtaining a porous sol-gel adsorbent material comprising at least
silane oxides;
an inorganic and/or organic acid having a boiling temperature of more than 100° C.;
a probe molecule with the following general formula (I)

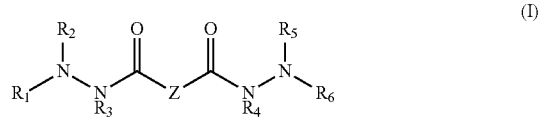

where $R_1$, $R_2$, $R_3$, $R_4$, $R_5$, $R_6$ independently represents a hydrogen atom, a (C1-C6) alkyl group, a (C3-C7) cycloalkyl group or an alkyl-(C3-C7) cycloalkyl group; and where Z represents a spacer group selected from a (C1-C16) alkyl group, a (C2-C16) alkenyl group, a (C2-C16) alkynyl group, a (C1-C16) haloalkyl group, an aryl group, an aryloxy group, a carbocyclic group and an aryl-(C1-C16) alkyl group.

What has been described above concerning the process according to the invention and relating to the acids and probe molecules likewise applies to the material according to the invention. Similarly, what has been described above concerning the alkoxysilane-type sol-gel precursor likewise applies to the silane oxide of the material according to the invention.

In the remainder of the text, the term "material" according to the invention is used indiscriminately to refer to the porous sol-gel adsorbent material according to the invention or to the material obtainable by the process according to the invention. The material according to the invention is also called silicate sol-gel matrices, i.e. sol-gel matrices obtained from metal alkoxides of the formula M (OR) xR'n-x where M is Si.

The silane oxides of the material according to the invention are those obtained after the hydrolysis/condensation reaction of the alkoxysilane type sol-gel precursors implemented in the process according to the invention and described above. The silane oxides of the material according to the invention are generally polysiloxanes, obtained after the hydrolysis/condensation reaction of the alkoxysilane type sol-gel precursors The adsorbent porous sol-gel material according to the invention may be in the form of cylindrically shaped granules with a ratio L/D>1 where L is the length of the granule and D is the diameter of the granule.

The invention also concerns the use of a material according to the invention, or a material likely obtainable by the process according to the invention for capturing aldehydes and/or ketones, in particular aldehydes selected from formaldehyde, acetaldehyde, propionaldehyde, butyraldehyde, acrolein, pentanal, hexanal, benzaldehyde and mixtures thereof.

Aldehyde refers to any organic molecule with a terminal carbonyl function preferably selected from formaldehyde, acetaldehyde, propionaldehyde, butyraldehyde, acrolein, pentanal, hexanal and benzaldehyde.

The invention also concerns an air purification device using a material according to the invention or a material obtainable by the process according to the invention.

When the polluted air passes through the porous adsorbent sol-gel material according to the invention, the pollutant reacts with the probe molecule to form a third chemical entity with a higher molecular weight which will remain trapped in the nanoporous network of the filter media comprising a specific adsorbent material. Unlike other adsorbents, this specific adsorbent material performs a definitive trapping through the irreversible chemical transformation of the pollutant. Without being tied to any theory, when, for example, an aldehyde or ketone comes into contact with the amino group(s) of the probe molecule, the carbonyl group reacts with the amine group to give an imine group. Generally speaking, this first reaction does not produce any coloring. In the presence of a high concentration of amino compounds and pollutants in the pores, this can induce further reactions that lead to a colored product. As an example, a yellow-orange color is obtained at saturation when the matrix according to the invention is exposed to formaldehyde or acetone and a reddish-brown color with benzaldehyde.

When the pollutants are large, such as benzaldehyde, the porosity of the sol-gel material allows rapid diffusion of the aldehydes/ketones in the matrix in order to trap them and make them react with the amino groups of the probe molecule and obtain a color change at saturation.

The material according to the invention is generally porous, preferably microporous, more preferably nanoporous or mesoporous, with a large specific surface area.

The nanoporous sol-gel materials according to the invention are characterized in particular in that they have a specific adsorption surface area of 15±2 to 900±100 m2·g-1, preferably 150±20 m2·g-1 to 900±100 m2·g-1. Advantageously, the microporous sol-gel materials according to the invention also present a specific adsorption surface of 500±50 m2·g-1 to 900±100 m2·g-1, preferably from 650±70 m2·g-1 to 900±100 m2·g-1 and even more preferably from 750±70 m2·g-1 to 900±100 m2·g-1. Mesoporous sol-gel materials according to the invention advantageously have a specific adsorption surface of 15±2 to 400±40 m2·g-1 and even more preferably from 150±20 m2·g-1 to 300±50 m2·g-1. The specific surface area and pore size distribution are determined through the analysis of the liquid nitrogen adsorption-desorption isotherm using the DFT (Density Functional Theory) model.

Thus the material according to the invention makes it possible to eliminate harmful pollutants such as formaldehyde, a molecule that conventional adsorbent materials cannot or hardly eliminate.

In one embodiment, the specific adsorbent material according to the invention may comprise a nanoporous sol-gel matrix of metal oxides, said matrix containing at least one probe molecule carrying at least one reactive function capable of reacting with an aldehyde function.

According to the invention, the depollution/filtration performance of the cartridge is determined in particular by the following parameters:—the proportion by mass between the adsorbent or conventional adsorbent material and the specific adsorbent material, the specific surface area of the specific adsorbent material,—the shape of the specific adsorbent material, the physical and chemical characteristics of the adsorbent or conventional adsorbent material.

The following examples illustrate the invention without limiting its scope.

EXAMPLES

Example 1: TMOS MATRIX Doped with Adipic Acid Dihydrazide and Sulphamic Acid (Formulation E1)

Reagents: Adipic acid dihydrazide (CAS No. 1071-93-8, molar mass=174.2 g·mol$^{-1}$, purity 98%), TMOS (CAS number: 681-84-5, molar mass=152.2 g·mol$^{-1}$, density d=1.023 mg·cm$^{-3}$), Sulphamic acid (CAS number 5329-14-6, molar mass=97.1 g g·mol$^{-1}$, technical grade purity). Plastic honeycomb mold with cylindrical shafts with a diameter of 6 mm and a depth of 10 mm.

V (TMOS)=1,463 mL
V (H$_2$O)=2,927 mL
adipic acid dihydrazide=90.5 g (0.12M)
sulphamic acid=51.2 g (0.12M)
V (total)=4,390 mL Operating Procedure: 90.5 g adipic acid dihydrazide and 51.2 g sulphamic acid are placed in a 5,000 mL bottle and 2,927 mL of water is added. The mixture is stirred until the adipic acid dihydrazide and sulphamic acid are completely dissolved. The aqueous solution is placed in a 5 L double-shell reactor thermostatically kept at 25° C. 1,463 mL of TMOS is added. The mixture is left under mechanical agitation. The formation of 2 phases can be observed. The mixture is left to stir until it becomes homogeneous (10 min). The mixture is poured into a PTFE tray fitted with a honeycomb mold. The tray is placed in a drying cabinet thermostatically controlled at 40° C. The tray is brushed with a flow of nitrogen (N$_2$) with a flow rate of 10 L/min. Drying is stopped after one or more days.

The dry granules obtained are translucent. These granules are rebaked at 70° C. for 4 hours.

In this example the molar proportions of the reagents TMOS/H$_2$O/adipic acid dihydrazide/sulphamic acid are equal to 1/16.5/0.052/0.054.

Example 2: TMOS Matrix Doped with Adipic Acid Dihydrazide and Sulphamic Acid (Formulation E2)

Reagents: Adipic acid dihydrazide (CAS number 1071-93-8, molar mass=174.2 g·mol$^{-1}$, purity 98%), TMOS (CAS number: 681-84-5, molar mass=152.2 g·mol$^{-1}$, density d=1.023 mg·cm$^{-3}$), sulphamic acid (CAS number 5329-14-6, molar mass=97.1 g g·mol$^{-1}$, technical grade purity). Plastic honeycomb mold with cylindrical shafts with a diameter of 6 mm and a depth of 10 mm.

V (TMOS)=1,463 mL
V (H$_2$O)=2,927 mL
adipic acid dihydrazide=30.2 g (0.04M)
sulphamic acid=17.1 g (0.04M)
V (total)=4,390 mL Operating Procedure: 30.2 g adipic acid dihydrazide and 17.1 g sulphamic acid are placed in a 5,000 ml bottle and 2,927 mL of water is added. The mixture is stirred until the adipic acid dihydrazide and sulphamic acid are completely dissolved. The aqueous solution is placed in a 5 L double-shell reactor thermostatically kept at 25° C. 1,463 mL of TMOS is added. The mixture is left under mechanical agitation. The formation of 2 phases can be observed. The mixture is left to stir until it becomes homogeneous (10 min). The mixture is poured into a PTFE tray fitted with a honeycomb mold. The tray is placed in a drying cabinet thermostatically controlled at 40° C. The tray is brushed with a flow of nitrogen (N$_2$) with a flow rate of 10 L/min. Drying is stopped after one or more days.

The dry granules obtained are translucent. These granules are rebaked at 70° C. for 24 hours.

In this example, the molar proportions of the reagents TMOS/H$_2$O/adipic acid dihydrazide/sulphamic acid are equal to 1/16.5/0.017/0.018.

Example 3: TMOS Matrix Doped with Adipic Acid Dihydrazide and Phosphoric Acid (Formulation E3)

Reagents: Adipic acid dihydrazide (CAS No. 1071-93-8, molar mass=174.2 g·mol$^{-1}$, purity 98%), TMOS (CAS number: 681-84-5, molar mass=152.2 g·mol$^{-1}$, density d=1.023 mg·cm$^{-3}$), phosphoric acid (CAS number 7664-38-2, molar mass=98 g·mol$^{-1}$, purity 85%). Plastic honeycomb mold with cylindrical shafts with a diameter of 6 mm and a depth of 10 mm.

V (TMOS)=1,446 mL
V (H$_2$O)=2,909 mL
adipic acid dihydrazide=90.5 g (0.12M)
phosphoric acid=35.52 mL (0.12M)
V (total)=4,390 mL Operating Procedure: 90.5 g adipic acid dihydrazide and 35.52 mL phosphoric acid are placed in a 5,000 mL vial and 2,909 mL of water are added. The mixture is stirred until the adipic acid dihydrazide and sulphamic acid are completely dissolved. The aqueous solution is placed into a 5 L double-shell reactor thermostatically kept at 25° C. 1,446 mL of TMOS is added. The mixture is left under mechanical agitation. The formation of 2 phases is observed. The mixture is left to stir until it becomes homogeneous (10 min). The mixture is poured into a PTFE tray fitted with a honeycomb mold. The tray is placed in a drying cabinet thermostatically controlled at 40° C. The tray is brushed with a flow of nitrogen (N$_2$) with a flow rate of 10 L/min. Drying is stopped after one or more days.

The dry granules obtained are translucent. These granules are rebaked at 70° C. for 24 hours.

In this example the molar proportions of the reagents TMOS/H$_2$O/adipic acid dihydrazide/phosphoric acid are equal to 1/16.5/0.052/0.054.

Example 4: TMOS MATRIX Doped with Adipic Acid Dihydrazide and Sulphamic Acid (Formulation E4)

Reagents: Adipic acid dihydrazide (CAS No. 1071-93-8, molar mass=174.2 g·mol$^{-1}$, purity 98%), TMOS (CAS number: 681-84-5, molar mass=152.2 g·mol$^{-1}$, density d=1.023 mg·cm$^{-3}$), MTMS (CAS number: 1185-55-3, molar mass=136.22 g·mol$^{-1}$, density d=0.955 mg·cm$^{-3}$), sulphamic acid (CAS number 5329-14-6, molar mass=97.1 g g·mol$^{-1}$, technical grade purity). Plastic honeycomb mold with cylindrical shafts with a diameter of 6 mm and a depth of 10 mm.

V (TMOS)=1,028 mL
V (MTMS)=423 mL
V (H$_2$O)=2,939 mL
adipic acid dihydrazide=90.5 g (0.12M)
sulphamic acid=51.2 g (0.12M)
V (total)=4,390 mL Operating Procedure: 90.5 g adipic acid dihydrazide and 51.2 g sulphamic acid are placed in a 5,000 mL bottle and 2.927 mL of water is added. The mixture is stirred until the adipic acid dihydrazide and sulphamic acid are completely dissolved. The aqueous solution is placed in a 5 L double-shell reactor thermostatically kept at 25° C. 1,028 mL of TMOS and 423 mL of MTMS are added. The mixture is left under mechanical agitation. The formation of 2 phases is observed. The mixture is left to stir until it becomes homogeneous (10 min). The mixture is poured into a PTFE tray fitted with a honeycomb mold. The tray is placed in a drying cabinet thermostatically controlled at 40° C. The tray is brushed with a flow of nitrogen (N$_2$) with a flow rate of 10 L/min. Drying is stopped after one or more days.

The dry granules obtained are translucent. These granules are rebaked at 70° C. for 24 hours.

In this example the molar proportions of the reagents TMOS/H$_2$O/adipic acid dihydrazide/sulphamic acid are equal to 1/16.5/0.3/0.052/0.054.

Example 5: TMOS MATRIX Doped with Adipic Acid Dihydrazide and Paratoluene Sulphonic Acid
(Formulation E5)

Reagents: Adipic acid dihydrazide (CAS No. 1071-93-8, molar mass=174.2 g·mol$^{-1}$, purity 98%), TMOS (CAS number: 681-84-5, molar mass=152.2 g·mol$^{-1}$, density d=1.023 mg·cm$^{-3}$), paratoluene sulphonic acid monohydrate (CAS number 6192-52-5, molar mass=190.2 g g·mol$^{-1}$, purity ≥98%). Plastic honeycomb mold with cylindrical shafts with a diameter of 6 mm and a depth of 10 mm.

V (TMOS)=1,463 mL
V (H$_2$O)=2,927 mL
adipic acid dihydrazide=45.25 g (0.06M)
paratoluene sulphonic acid monohydrate=52.9 g (0.06M)
V (total)=4,390 mL Operating Procedure: 90.5 g adipic acid dihydrazide and 52.9 g paratoluene sulphonic acid monohydrate are placed in a 5,000 mL bottle and 2,927 mL of water is added. The mixture is stirred until the adipic acid dihydrazide and paratoluene sulphonic acid monohydrate are completely dissolved. The aqueous solution is placed in a 5 L double-shell reactor thermostatically kept at 25° C. 1,463 mL of TMOS is added. The mixture is left under mechanical agitation. The formation of 2 phases is observed. The mixture is left to stir until it becomes homogeneous (10 min). The mixture is poured into a PTFE tray fitted with a honeycomb mold. The tray is placed in a drying cabinet thermostatically controlled at 40° C. The tray is brushed with a flow of nitrogen (N$_2$) with a flow rate of 10 L/min. Drying is stopped after one or more days.

The dry granules obtained are translucent. These granules are rebaked at 70° C. for 24 hours.

In this example the molar proportions of the reagents TMOS/H$_2$O/adipic acid dihydrazide/paratoluene sulphonic acid monohydrate are equal to 1/16.5/0.026/0.027.

Example 6: TMOS MATRIX Doped with Terephthalic Acid Dihydrazide and Sulphamic Acid
(Formulation E6)

Reagents: Terephthalic acid dihydrazide (CAS No. 136-64-1, molar mass=194.194 g·mol$^{-1}$), TMOS (CAS number: 681-84-5, molar mass=152.2 g·mol$^{-1}$, density d=1.023 mg·cm$^{-3}$), Sulphamic acid (CAS number 5329-14-6, molar mass=97.1 g g·mol$^{-1}$, technical grade purity. Plastic honeycomb mold with cylindrical shafts with a diameter of 6 mm and a depth of 10 mm.

V (TMOS)=1,463 mL
V (H$_2$O)=2,927 mL
terephthalic dihydrazide=25.58 g (0.03M)
sulphamic acid=25.58 g (0.06M)
V (total)=4,390 mL Operating Procedure: 25.58 g of terephthalic acid dihydrazide and 25.58 g of sulphamic acid are placed in a 5,000 mL bottle and 2,927 mL of water is added. The mixture is stirred until the terephthalic acid dihydrazide and sulphamic acid are completely dissolved. The aqueous solution is placed in a 5 L double-shell reactor thermostatically kept at 25° C. 1,463 mL of TMOS is added. The mixture is left under mechanical agitation. The formation of 2 phases is observed. The mixture is left to stir until it becomes homogeneous (10 min). The mixture is poured into a PTFE tray fitted with a honeycomb mold. The tray is placed in a drying cabinet thermostatically controlled at 40° C. The tray is brushed with a flow of nitrogen (N$_2$) with a flow rate of 10 L/min. Drying is stopped after one or more days.

The dry granules obtained are translucent. These granules are rebaked at 70° C. for 24 hours.

In this example the molar proportions of the reagents TMOS/H$_2$O/terephthalic acid dihydrazide/sulphamic acid are equal to 1/16.5/0.013/0.027.

Example 7: TMOS MATRIX Doped with Sebacic Acid Dihydrazide and Sulphamic Acid
(Formulation E7)

Reagents: Sebacic acid dihydrazide (CAS No. 925-83-7, molar mass=230.31 g·mol$^{-1}$), TMOS (CAS number: 681-84-5, molar mass=152.2 g·mol$^{-1}$, density d=1.023 mg·cm$^{-3}$), sulphamic acid (CAS number 5329-14-6, molar mass=97.1 g g·mol$^{-1}$, technical grade purity). Plastic honeycomb mold with cylindrical shafts with a diameter of 6 mm and a depth of 10 mm.

V (TMOS)=1,463 mL
V (H$_2$O)=2,927 mL
sebacic acid dihydrazide=30.33 g (0.03M)
sulphamic acid=25.58 g (0.06M)
V (total)=4,390 mL Operating Procedure: 30.33 g of sebacic acid dihydrazide and 25.58 g of sulphamic acid are placed in a 5,000 mL bottle and 2,927 mL of water is added. The mixture is stirred until the sebacic acid dihydrazide and sulphamic acid are completely dissolved. The aqueous solution is placed in a 5 L double-shell reactor thermostatically kept at 25° C. 1,463 mL of TMOS is added. The mixture is left under mechanical agitation. The formation of 2 phases is observed. The mixture is left to stir until it becomes homogeneous (10 min). The mixture is poured into a PTFE tray fitted with a honeycomb mold. The tray is placed in a drying cabinet thermostatically controlled at 40° C. The tray is brushed with a flow of nitrogen (N$_2$) with a flow rate of 10 L/min. Drying is stopped after one or more days.

The dry granules obtained are translucent. These granules are rebaked at 70° C. for 24 hours.

In this example the molar proportions of the reagents TMOS/H$_2$O/sebacic acid dihydrazide/sulphamic acid are equal to 1/16.5/0.013/0.027.

Measurement of the Trapping Capacity of Formulations E1 to E7.

The materials to be tested were exposed to formaldehyde concentrations of about 400 ppbv at a flow rate of 4 l/min. These conditions were obtained using the ETHERA generation bench shown in FIG. 1.

Formaldehyde is generated in a permeation oven with regulated temperature and nitrogen flow. The formaldehyde obtained at contents in the order of several ppmv is diluted by a flow of dry compressed air and another of wet compressed air (HR ≈100%) in order to obtain an air flow calibrated at 400 ppbv formaldehyde and 50% humidity. This gas flow is then separated into three streams and sent to sampling tanks B1, B2 and B3. On the lines leading to B2 and B3 are test cartridges containing the materials to be studied. The formaldehyde-polluted gas therefore passes through the cartridges before arriving in the B2 and B3 tanks.

Once or twice a day a gaseous sample is taken from each of the tanks to determine the formaldehyde concentrations passing through each of them. The value obtained for B1 gives us the formaldehyde concentration upstream of the test cartridges whereas the values obtained for B2 and B3 give us the concentrations downstream of the test cartridges. The formaldehyde concentrations are determined using the Profil'air Dynamic kit method.

The average concentration upstream and downstream of the cartridges is determined for each measuring point, and these concentrations are converted into the formaldehyde mass per minute that arrives upstream of the cartridges and exits downstream. The difference between these two values determines the mass of the formaldehyde trapped per minute of exposure.

To calculate the quantity of formaldehyde trapped, a linear evolution of the amount trapped as a function of time is assumed between each measuring point. The corresponding line between the two points is drawn and its equation is determined. This equation is then integrated between the two measuring points to determine the area under the line and thus the amount of formaldehyde trapped between the two measuring points. The sum of the areas thus determined represents the total quantity of formaldehyde trapped during the test period.

The trapping capacity of each porous sol-gel material obtained, formulations E1 to E7. was determined:

| Formulation | Trapping capacity (mg/g) |
| --- | --- |
| E1 | 11.1 |
| E2 | 3.2 |
| E3 | 7.0 |
| E4 | 6.5 |
| E5 | 5.3 |
| E6 | 3.1 |
| E7 | 7.2 |

The invention claimed is:

1. An air purification device comprising a porous sol-gel adsorbent material comprising:
   a silane oxide;
   at least one acid of paratoluenesulphonic acid or parahydroxybenzoic acid; and
   a probe molecule represented by the following General Formula (I) or a salt thereof,

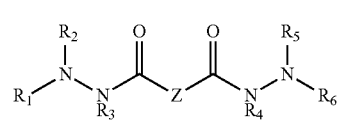

[General Formula I)]

wherein $R_1$, $R_2$, $R_3$, $R_4$, $R_5$, and $R_6$ each independently represent a hydrogen atom, a (C1-C6) alkyl group, a (C3-C7) cycloalkyl group or an alkyl-(C3-C7) cycloalkyl group, and
   Z represents a spacer group selected from the group consisting of a (C1-C16) alkyl group, a (C2-C16) alkenyl group, a (C2-C16) alkynyl group, a (C1-C16) haloalkyl group, an aryl group, an aryloxy group, a carbocyclic group, and an aryl-(C1-C16) alkyl group.

2. The air purification device of claim 1, wherein the air purification device does not comprise zeolite.

3. The air purification device of claim 1, wherein the air purification device does not comprise activated carbon.

* * * * *